(12) United States Patent
Cabeza et al.

(10) Patent No.: US 7,744,217 B2
(45) Date of Patent: Jun. 29, 2010

(54) APPARATUS AND METHOD FOR DETERMINING AN EYEGLASS PRESCRIPTION FOR A VISION DEFECT OF AN EYE

(75) Inventors: Jesus Miguel Guillen Cabeza, Aalen (DE); Timo Kratzer, Aalen (DE)

(73) Assignee: Carl Zeiss Vision GmbH, Aalen (DE)

( * ) Notice: Subject to any disclaimer, the term of this patent is extended or adjusted under 35 U.S.C. 154(b) by 303 days.

(21) Appl. No.: 11/840,688

(22) Filed: Aug. 17, 2007

(65) Prior Publication Data
US 2009/0015787 A1 Jan. 15, 2009

(30) Foreign Application Priority Data
Jul. 9, 2007 (DE) ........................ 10 2007 032 001

(51) Int. Cl.
*A61B 3/10* (2006.01)
*G02C 5/00* (2006.01)

(52) U.S. Cl. .................. 351/205; 351/41; 351/221; 351/246

(58) Field of Classification Search ............ 351/41, 351/200, 205, 221, 246–247
See application file for complete search history.

(56) References Cited

U.S. PATENT DOCUMENTS

| | | | |
|---|---|---|---|
| 4,105,302 A | 8/1978 | Tate, Jr. | |
| 6,048,064 A | 4/2000 | Hosoi et al. | |
| 6,382,795 B1 | 5/2002 | Lai | |
| 6,406,146 B1 | 6/2002 | Lai | |
| 6,511,180 B2 | 1/2003 | Guirao et al. | |
| 6,575,572 B2 | 6/2003 | Lai et al. | |
| 6,997,555 B2 | 2/2006 | Dick et al. | |
| 7,029,119 B2 | 4/2006 | Youssefi et al. | |
| 7,084,986 B2 | 8/2006 | Hellmuth et al. | |
| 7,547,102 B2 * | 6/2009 | Dai .......................... 351/205 | |
| 2003/0038921 A1 | 2/2003 | Neal et al. | |
| 2004/0008323 A1 | 1/2004 | Williams | |
| 2004/0100619 A1 | 5/2004 | Olivier et al. | |
| 2004/0169820 A1 | 9/2004 | Dai et al. | |
| 2005/0174535 A1 * | 8/2005 | Lai et al. ..................... 351/205 | |

(Continued)

FOREIGN PATENT DOCUMENTS

DE 601 21 123 2/2007

(Continued)

OTHER PUBLICATIONS

Power Point presentation entitled "A tutorial on higher order aberrations: What are they? How are they measured? What is their clinical relevance? Can they be corrected?," presented by Louis J. Catania, O.D., F.A.A.O., 2003.

(Continued)

*Primary Examiner*—Scott J Sugarman
*Assistant Examiner*—Dawayne A Pinkney
(74) *Attorney, Agent, or Firm*—Fish & Richardson P.C.

(57) ABSTRACT

The disclosure relates to a method for determining an eyeglass prescription for a vision defect of an eye. In certain embodiments, the method includes optimizing a caustic in the area of the retina of the eye for a light ray passing through the eyeglass prescription and the eye. The disclosure further relates to an apparatus that is suitable for carrying out the method.

37 Claims, 2 Drawing Sheets

U.S. PATENT DOCUMENTS

| | | | |
|---|---|---|---|
| 2005/0179861 A1 | 8/2005 | Kitani et al. | |
| 2006/0023162 A1 | 2/2006 | Azar et al. | |
| 2006/0197911 A1* | 9/2006 | Williams | 351/205 |
| 2006/0279699 A1 | 12/2006 | Liang | |
| 2008/0100800 A1* | 5/2008 | Guillen et al. | 351/205 |
| 2008/0231802 A2 | 9/2008 | Cabeza et al. | |

FOREIGN PATENT DOCUMENTS

| | | |
|---|---|---|
| EP | 1 324 689 | 8/2006 |
| EP | 1 324 689 B1 | 8/2006 |
| WO | WO 01/89372 | 11/2001 |
| WO | WO 02/083078 | 10/2002 |
| WO | WO 2004/072687 | 8/2004 |
| WO | WO 2004/096014 | 11/2004 |

OTHER PUBLICATIONS

Power Point presentation entitled "Vision Optimized Spectacles and Contact Lenses," presented by Jerome A. Legerton, OD, MS, MBA, FAAO, 2004.

Power Point presentation entitled "Clinical Results for Wavefront Corrected Spectacle Lenses," presented by Perry S. binder, MD, 2004.

* cited by examiner

APPARATUS AND METHOD FOR DETERMINING AN EYEGLASS PRESCRIPTION FOR A VISION DEFECT OF AN EYE

CROSS-REFERENCE TO RELATED APPLICATIONS

This application claims priority under 35 U.S.C. §119 to German Patent Application Serial No. 10 2007 032 001.0, filed on Jul. 9, 2007, the contents of which are hereby incorporated by reference.

FIELD OF THE INVENTION

The invention relates to methods for determining the eyeglass prescription for the vision defect of an eye as well as suitable apparatus for determining the eyeglass prescription for the vision defect of an eye. Lastly, the invention also relates to computer programs, computer software products, and computers for executing methods according to the invention.

BACKGROUND

The vision-impaired human eye has refractive errors which in first approximation can be described in terms of a sphere, a cylinder and an axis orientation. This is based on the assumption that the eyesight defect can be approximately corrected through a lens with a toroidal surface. This approximation is adequate to correct an error in the refraction of light rays which fall on the center of the eye pupil.

While it was customary in the past to determine the refractive errors of the human eye by relying on the subjective reaction of the patient under examination when presenting to him a plurality of optotypes of different refractive power (subjective refraction), the possibility of measuring the refractive errors of the eye has now been available for several years (objective refraction). It is possible to measure the refractive power of the eye over the entire pupil and in particular also in the peripheral areas of the pupil. The measurable errors include for example spherical aberration, coma, trefoil error, higher orders of spherical aberration, etc. The objective refraction method is based on determining the wavefront of a propagating light bundle. The functional principal of a wavefront refractor is described in DE 601 21 123 T2, which also includes a synopsis of a plurality of different variants.

It has been customary for a few years to describe the refractive errors or imaging errors of the human eye by means of so-called Zernike polynomials. The errors of the eye near the center in regard to sphere, cylinder and axis can be described through second-order Zernike polynomials. These errors are therefore often referred to as second-order errors. The errors far from the center can be described through higher-order Zernike polynomials. These errors are therefore in general also referred to as higher-order errors.

The information gained from a wavefront refractor can be used in the development of improved vision aids or improved eyesight correction methods. A well-known example for an eyesight correction method is the procedure of wave-front-guided refractive surgery. In this procedure, a volume of any desired geometry is removed from the surface of the cornea in order to correct refractive errors, including those of a higher order.

With vision aids such as for example a spectacle lens or a contact lens, this kind of correction is not generally possible at all or possible only under certain conditions. A spectacle lens has the peculiar property that the line of vision from the eye has to pass through different areas of the lens. A complete correction of higher-order errors in a spectacle lens is generally possible only for one specific direction of the line of vision. As soon as the eye looks in another direction, the correction no longer matches the higher-order errors, which lowers the vision performance. Furthermore, a complete correction of higher-order errors in a spectacle glass may lead to unacceptable distortions outside the area of correction.

However, the wave-front measurement technique can nevertheless lead of improved spectacle lenses.

The subjective refraction is conventionally performed under daylight conditions with high-contrast optotypes. This leads to refraction values which are optimized for these conditions, i.e. for a good illumination and for a high level of contrast. For many individuals, this method of refraction is not suitable for night vision or twilight vision. A wavefront measurement, on the other hand, can be performed in the dark or under mydriatic conditions. This provides the information for a much larger pupil, which opens the possibility to obtain an objective refraction result (in particular for a second-order refraction) which is also suitable for mesopic or scotopic light conditions.

Spectacle lenses, in particular progressive lenses, can have intrinsic aberrations. These intrinsic aberrations can be combined with the wavefront measurement taken for the eye, as a means to compute and manufacture improved spectacle lenses. These spectacle lenses can make it possible to at least partially correct the higher-order aberrations of the optical system constituted by the eye and the spectacle lens for at least one specific direction of the line of vision.

The determination of an improved second-order and higher-order refraction result from the wavefront measurement is known from the prior art in a multitude of variations. A concept of deriving the second-order refraction from the averaged main curvatures of the wavefronts is disclosed in U.S. Pat. No. 7,029,119.

A system for determining a correction of aberrations in an eye of a patient is described for example in EP 1 324 689 B1. The system includes a computing device which allows the correction of the data signals to be determined in such a way that, if the correction is applied to the eye, an image quality metric in an image plane of the eye is objectively optimized. In a first step, the computing device defines a search space (i.e., values that can be assumed by the coefficients), which covers several sets of coefficients (e.g., sphere, cylinder, axis, or the corresponding Zernike coefficients). In a second step, the previously selected image quality metric (e.g., Strehl ratio, variance of point image washout function, energy of the point image washout function enclosed within the Airy disc, etc.) is calculated for each of the sets of coefficients in the search space (i.e., the corresponding dioptric values for defocus and astigmatism, as well as the associated axis orientation). In a third step, the optimal value of the image quality metric is selected from all of the values of the image quality metric that were calculated in the second step, and in a fourth step, the correction is determined in conformance with one of the several sets of coefficients for which the optimal value of the image quality metric was calculated in the third step.

In their essay "Accuracy and precision of objective refraction from wavefront aberration", which was published in Journal of Vision (2004) 4, 329-351, on Apr. 23, 2004, L. N. Thibos et al. describe a multitude of further objective methods for the determination of the refraction from a wavefront measurement.

SUMMARY

The methods described above for the determination of the subjective or objective refraction generally disregard the physiology of the eye. The eye is not a static system like the classic optical systems. It possesses the ability of accommodation. In the process of accommodation, the human lens changes its shape as well as its position in order to change the overall refractive power of the eye. The process of accommodation is a continuous process in which the system constituted by the eye and the brain is continuously seeking stimuli in order to always generate the best image. This means that the entire refractive power of the eye is subject to high-frequency changes. The aberration structure of the eye also changes with the accommodation of the eye. In particular the spherical aberration becomes on average more negative with accommodation. A pair of glasses matched to the objective or subjective refraction value is therefore often not perceived as optimal by the wearer.

Methods and apparatus for the determination of a eyeglass prescription for the impaired vision of an eye are disclosed, which take into account the physiology of the eye in the calculation of a vision correction, based for example on a wavefront measurement of the eye. An eyeglass prescription in this context means in particular the optical power of a spectacle lens or a contact lens, and also the extent of a local removal of natural component matter of the vision-impaired eye.

According to another aspect of the invention, the procedure for determining the eyeglass prescription for the impaired vision of an eye includes mathematically varying a preliminary prescription within a target space or search space. It is not necessary for this target space or search space to be known at the outset. It is possible to vary the preliminary prescription until a criterion for terminating the process has been met. A termination criterion can for example be constituted by the attainment of an optimum or of a value that is very close to the optimum of a target criterion which will be described in the following.

The preliminary prescription which is selected within the target space is that prescription for which the caustic of a light beam passing through a corrective optic (e.g., a lens or lenses) corresponding to the eyeglass prescription and that satisfies specific given requirements in the retinal area of the eye. The term "caustic" in this context means the more or less narrow constriction which occurs instead of an image point as a result of imaging errors for a light bundle originating from an object point before it spreads out again.

The given requirements that are to be met may spell out that a metric describing the quality of the caustic has to exceed a certain threshold value or lie within a given range around an optimal value.

In some aspects, apparatus for the determination of the eyeglass prescription includes an analyzer device which serves to select the eyeglass prescription within the search space as that eyeglass prescription for which the caustic of a light beam passing through an optic corresponding to the eyeglass prescription and the eye satisfies the abovementioned specific given requirements in the retinal area of the eye.

In concrete terms, methods for determining the eyeglass prescription for the vision defect of an eye a can include the following steps:

In a first step, the refractive properties of the eye are established. At this stage, the eye can be in a specific prescribed state of accommodation. For example, the eye can be focused on infinity, meaning that the rays of vision of the eyes do not converge in a point at a near distance.

The refractive properties of the vision-impaired eye can be determined for example at the outset by measuring the wavefront of the eye to be corrected. In professional terminology, this process is referred to as "establishing a wavefront aberration map". In concrete terms, this wavefront measurement can be performed by means of the so-called Shack-Hartmann method or by means of the so-called Tscherning method. These methods are based, respectively, on the projection of a light ray (Hartmann-Shack) or of a light point pattern (Tscherning) on the retina. The path of the reflected ray in the optical system is investigated under wavefront conditions. Changes in the direction of the rays or, respectively, a deviation of the image from the original pattern after leaving the optical system are registered. The deviation of the profile of this wavefront from the ideal case is referred to as aberration and can be measured with an aberrometer. In general, the Hartmann-Shack method can use a CCD camera for the recording of the image. Details of this process can be found for example in the dissertation of G. M. Spitzlberger, "Änderungen der optischen Aberrationen des menschlichen Auges durch laser in situ keratomileusis" (*Changes of the optical aberrations of the human eye caused by laser-assisted in situ keratomileusis*), published in 2004.

Instead of a wavefront analysis of the kind described above, it is also possible to make use of the so-called ray-tracing method for the determination of the refractive aberrations of the vision-impaired eye. In this method, a very fine laser beam is directed through the pupil of the eye and scanned over the retina. Each laser point can be identified as a reflection on the macula. The position and shape of this image on the macula allows certain conclusions to be drawn about the refraction and the vision quality.

Finally, the refractive properties of the (e.g., human or animal) eye can also be determined by measuring the tomography of the eye. In concrete terms, the geometries of the surfaces of the eye that perform an optical function are measured. This may also include measuring the refractive indices of the individual media.

In a second step, the values of parameter sets describing the eyeglass prescription are determined. These values can include, e.g., sphere, cylinder and axis. It is also possible that the values include so-called surface descriptions or subsets of surface descriptions such as splines, Taylor series, or Zernike expansions, and more specifically individual coefficients of these expansions.

The computer capabilities make it possible to define the eyeglass prescription through the values of the coefficients of an algebraic representation of a basis or surface that is suitable to describe the eyeglass prescription, for example through spline-, Zernike- or Taylor coefficients.

As a third step, a suitable method is established for determining from the parameter sets a set of target parameters which provides for the refractive properties of the eye that were established or determined in the first step an optimal eyeglass prescription that meets the specified requirements. In the following, this eyeglass prescription will be referred to as target eyeglass prescription or—in the case of an optimizing process as will be described below—as optimal eyeglass prescription.

Methods that can be suitable include for example a Newton-Raphson method, a hill-climbing method, or a "try-anything" method, where within a search space of parameter sets, all of the sets in the space are examined against the given requirements, in particular with a view to finding an optimum.

It should be noted that the three steps described above are not meant to define a sequence in time, as it is irrelevant which of the three steps is carried out first, and in what sequence the associated data are established. It matters only that the data are made available for the process of determining the target eyeglass prescription which follows below, in particular for the optimal eyeglass prescription.

In a (e.g., subsequent) fourth step, at least two submetrics can be determined for one of the parameter sets in different stages of the propagation of light through the optical system represented by the eye and an optic corresponding to the eyeglass prescription. In other words, the light passes through the optical system represented by the eye and the optic. One now considers the deviation of the light ray compared to the ideal case, as expressed through a quality metric (submetric), when the light ray has traversed (propagated through) the system represented by the eye and the correction by different travel distances. A propagation in the reverse direction, e.g., directed from the system represented by the eye and the optic towards the object, is likewise conceivable. The propagation being considered here is not tied to a fixed direction through the system represented by the eye and the correction, but can be carried out for any desired number of directions (e.g., in general directions of the line of sight).

In the literature (e.g., L. N. Thibos et al. in the publication quoted above) there is often a distinction made between pupil plane metrics and image plane metrics. Those acquainted with this field will understand that, principally, both kinds of quality metrics can be used as submetrics.

Thus, these submetrics can include for example ray quality metrics such as for example metrics that measure the Strehl ratio or the energy of the point-image wash-out function enclosed within the Airy disc. It is also possible that the submetrics are geometric metrics such as for example those that take the mean curvature of the wavefront into account.

It is also possible to take into account the neuronal signal-processing of the image taken in by the human eye, as discussed for example also in L. N. Thibos et al. on page 330, half-way down the right-hand column with references to several further places in the literature.

In a subsequent fifth step, an overall metric which reflects in particular the quality of the caustic ("caustic metric") is determined from a weighted sum of the previously determined submetrics. In some embodiments, all submetrics are given equal weight in the determination of the overall metric (caustic metric). In certain embodiments, a submetric of a preferred propagation stage is weighted more heavily than the submetrics in the propagation stages before and/or behind this preferred propagation stage. If one uses for example submetrics that take the image quality in different planes into account, then the submetric for the image on the retina (which corresponds to the submetric in the preferred propagation stage) would preferably be given more weight than the submetric for an image before or behind the retina of the eye. The weight ratio could be for example 60/40.

If one uses more than two or three submetrics in different stages of the propagation, the submetrics in the propagation stages before and/or behind the preferred propagation stage can be given less weight with increasing distance from the preferred propagation stage. Assuming an example of submetrics that take the image quality in different planes into account (see above), the submetric for the image on the retina (which corresponds to the submetric in the preferred propagation stage) would preferably be given more weight than the submetric for an image at a distance of 0.5 dpt before or behind the retina of the eye. The submetric for an image at a distance of 0.5 dpt before or behind the retina, in turn, would be given more weight than the submetric for an image at a distance of 1 dpt before the retina.

The relative weights assigned could be for example 50/30/20, if no submetric ahead of the retina is considered, but two further submetrics in two different image planes behind the retina flow into the calculation. It is likewise possible that for a propagation in the direction towards the object the object plane is taken as the preferred stage of propagation.

In some embodiments, the intensity distribution in the three-dimensional space of the ray bundle is calculated by means of a modified Nijboer-Zernike formalism (continuum of submetrics) and the energy density along this intensity distribution is used as a parameter for the determination of the target parameter set, in particular for optimizing the optimal parameter set.

In a next-following sixth step, the steps four and five are performed for all of the parameter sets that are needed for the determination of the target parameter set according to the procedure provided in step three.

In the seventh step, the target parameter set which provides the overall target metric (target caustic metric) that satisfies the given requirements is selected from the parameter sets for which the steps four and five were carried out. For example, the optimal overall metric is in general the metric with the maximum value, or a value which deviates from the latter by an insignificant amount.

These method steps can be performed for different states of accommodation of the eye. If this has been done, a final target parameter set is calculated in a next-following step, which provides the final overall target metric (e.g., the final optimal overall metric) based on the relative weights given to all of the previously determined overall target metrics (e.g., optimal overall metrics) for the different states of accommodation of the eye.

In an eighth step, the eyeglass prescription is determined based on the (final) target parameter set (e.g., optimal [final] parameter set) selected in step seven or, if applicable, for different states of accommodation of the eye.

In embodiments, apparatus for the determination of the eyeglass prescription for the impaired vision of an eye can include an input device to provide the refractive properties of the eye, as well as an analyzer device (e.g., an electronic processor, such as a computer). The analyzer device has the function to first determine, for a parameter set of the quantities that describe the eyeglass prescription, at least two submetrics in different associated propagation stages of a light ray passing through the optical system that includes the eye and an optic corresponding to the eyeglass prescription. Based on a weighted sum of the submetrics, the analyzer device next determines an overall metric. This process of determining submetrics followed by a computation of an overall metric is repeated by the analyzer device for further parameter sets of the quantities describing the eyeglass prescription, which are needed to determine a target parameter set (for example an optimal parameter set). The analyzer device can be further equipped for the function of selecting the target parameter set (e.g., optimal parameter set) which provides the overall target metric (e.g., optimal overall metric) from the parameter sets for which the process of determining the submetrics and the subsequent calculation of an overall metric were performed. The analyzer device is further equipped for the function of determining the eyeglass prescription based on the target parameter set (e.g., optimal parameter set) that was selected in the preceding step. The apparatus can includes an output device that serves to deliver the information defining the eyeglass prescription in a user-accessible format.

The input device can include for example a keyboard through which data about the refractive properties of the eye can be entered which were determined by a wavefront measurement.

As an alternative or an addition, the input device can be connected through an appropriate interface to a wavefront-measuring device serving to measure the refractive properties of the eye (wavefront refractor) and/or to an aberrometer according to the Shack-Hartmann principle and/or to an aberrometer for the Tscherning method and/or to a tomograph for the eye and/or to an aberrometer operating according to the ray-tracing method.

Further proposed are a computer program, a computer software product, and a computer for executing the computer program in order to carry out methods discussed herein.

Embodiments are disclosed hereinafter in more detail. Components that are identical or serve the same function are marked with the same reference symbols in all of the drawing figures, wherein:

DETAILED DESCRIPTION

Figure 1:
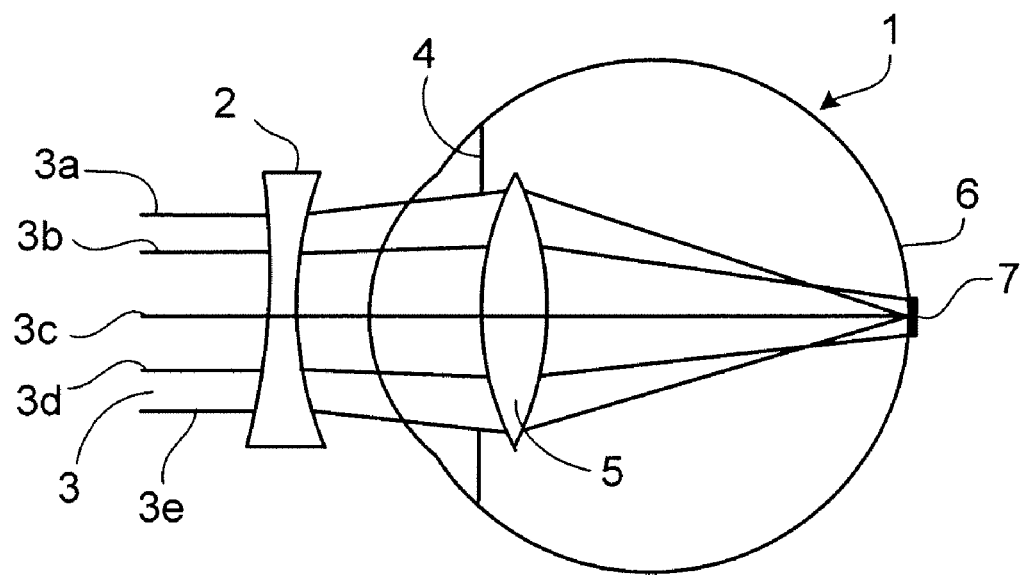
FIG. 1 represents a vision-impaired human eye with a spectacle lens, wherein the refractive properties of the spectacle lens are selected in the conventional manner in such a way that an image quality metric on the retina of the eye is optimized objectively.

FIG. 1 illustrates in cross-section a vision-impaired human eye with a spectacle lens 2. A bundle 3 of parallel light rays $3a$, $3b$, $3c$, $3d$, $3e$ enters through the spectacle lens 2 into the eye 1. The iris 4 delimits the incident light quantity. Because of the non-ideal refractive power of the optical system that is composed of the spectacle lens 2 and the eye lens 5, the light rays $3a$, $3b$, $3c$, $3d$, $3e$ form a non-ideal image on the retina 6 of the eye 1.

The second-order refraction of the spectacle lens 2 can be selected in such a way that the lens delivers an optimal image in an image plane, preferably in the retinal plane 7. This method can have the consequence that the image quality declines very rapidly outside of this plane. For example with strong spherical aberrations, such a decline can be very steep. This would translate into an extraordinary amount of effort for the eye, as the accommodation of the eye needs to be very precise in order to obtain a good image quality.

Figure 2:
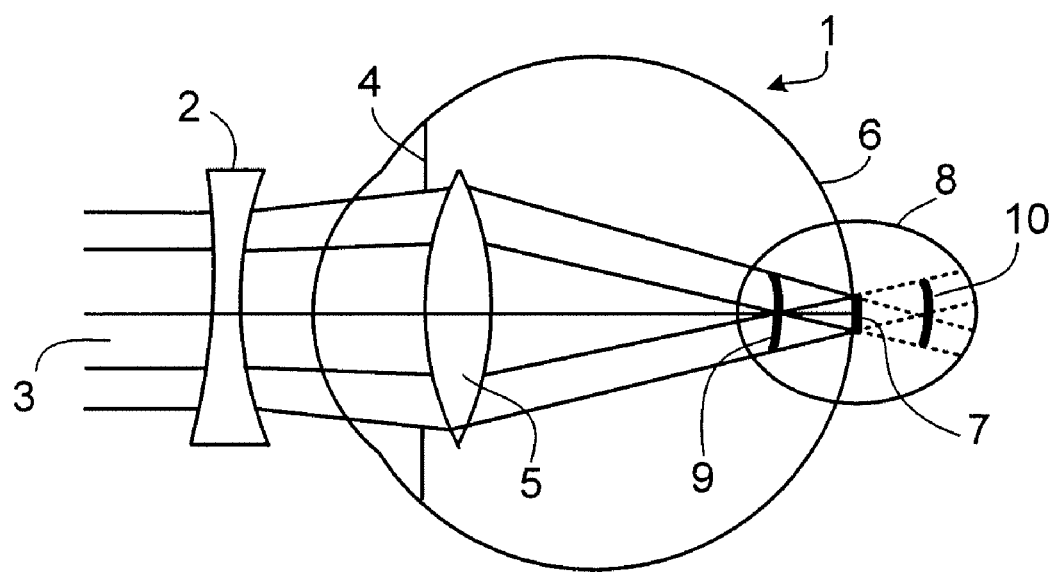
FIG. 2 represents a vision-impaired human eye with a spectacle lens, wherein the refractive properties of the spectacle lens are selected in such a way that the caustic of an incident light bundle entering the eye is optimized objectively in the area of the retina of the eye.

Optimizing the caustic 8 of the light bundle 3 in the area of the image plane 7, i.e., the plane of the retina 6 on which the light bundle forms an image (see FIG. 2), can solve this problem. Optimizing the caustic 8 in this region can offer for example the possibility to increase the depth of field of the image. At the same time, the image quality in the image plane 7 itself can be slightly reduced in relation to the achievable optimum. In return, this measure provides a more agreeable and trouble-free perception of one's eyesight, because fluctuations of the eye are eliminated.

The optimization of the caustic can be carried out for example as follows:

First, a so-called wavefront aberration map is determined for the eye which is in a given state of accommodation. In other words, a wavefront measurement is made for a certain given pupil surface.

Figure 3:
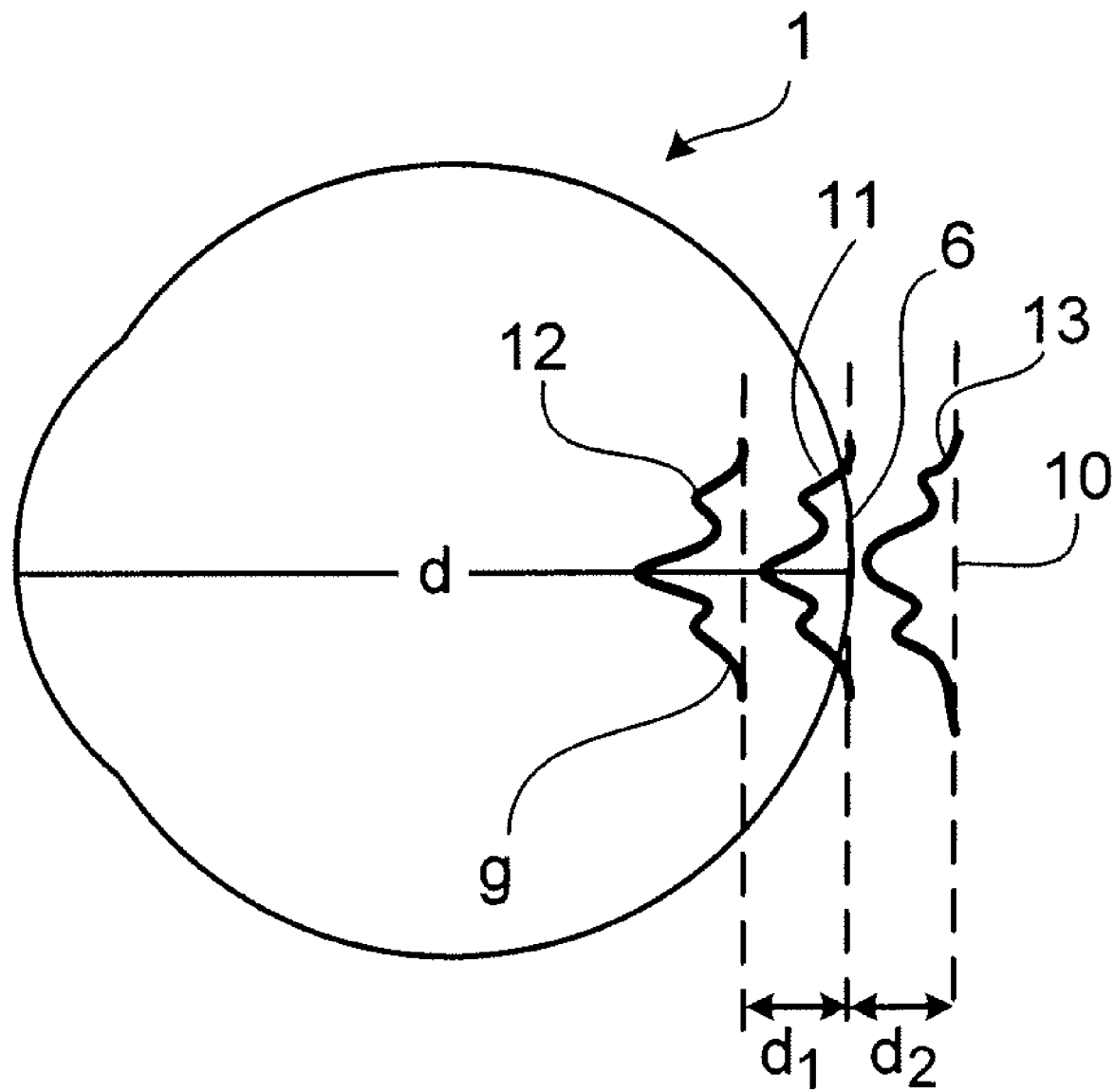
FIG. 3 represents the human eye according to FIG. 2 with a schematic representation of the point-image wash-out function in different propagation stages of the light.

Next, a search space of sets of quantities describing the eyeglass prescription is determined, such as sphere, cylinder, and axis. Continuing further, for each set of the search space, an image quality metric is determined which represents the image quality in the image plane 7 of the eye 1 resulting from applying the lens 2 having the eyeglass prescription to the eye 1. In the same manner the image quality metrics are determined in a plane 9 in front of the image plane 7 of the eye 1 and in a plane 10 behind the image plane 7 of the eye 1 for each set within the search space. The plane 9 can for example lie at a distance $d_1 = \frac{1}{2}$ dpt ($\approx 0.3$ mm) before the retina 6, and the plane 10 at about $d_2 = -\frac{1}{2}$ dpt ($\approx 0.3$ mm) behind the retina 6. The standard eye has a dimension d of about 43 dpt (=2.47 mm). To visualize this concept, FIG. 3 shows the point image wash-out functions 11, 12, 13 in the aforementioned plane 7, 9, 10 of a human eye 1.

By assigning appropriate weights to the image quality metrics in the different plane 7, 9, 10, a caustic metric representing a measure for the caustic in the area of the three planes 7, 9, 10 is calculated for every parameter set within the search space. This caustic metric is therefore a measure for the goodness of the caustic for the respective parameter set.

Based on all of the calculated overall metrics, whose number corresponds to the number of sets within the search space, one now selects an optimal overall metric, i.e., the caustic with the highest degree of goodness. Finally, the eyeglass prescription, i.e., the refractive power distribution of the spectacle lens 2 or the wavefront of the spectacle lens 2 is determined by taking the parameter set into account that led to the selected optimal overall metric.

Instead of determining a wavefront aberration map for an individual state of accommodation of an eye, it is also possible to determine aberration maps for a plurality of accommodation states and to perform the foregoing procedure for all of the accommodation states. The optimization process of the foregoing description can thus be improved by using not only the wavefront of the eye for the far distance. In referring to a wavefront measurement, one normally means the wavefront of an eye that is accommodated to infinity. However, it is also possible to measure the wavefront of the eye in different states of accommodation. As a result, a set of wavefronts of the eye is obtained. The forgoing process of optimization can be repeated for different wavefronts with different states of accommodation. This results in an eyeglass prescription which besides the far-distance optimization simultaneously includes a near-distance optimization.

It is further possible, for example, to rely only on the image quality metrics before and behind the retinal plane and to derive from them an overall metric.

Instead of determining a plurality of image quality metrics in different sectional planes and calculating a mean value representing an overall metric, it is also possible, for example, to determine the quality of the caustic around the image plane through ray tracing under the assumption of a suitable model for the eye.

For the evaluation of the quality of the caustic, different metrics can be used, for example the diameter of the caustic that encloses more than a certain proportion of the energy, or the proportion of the energy that falls within a certain area around the optical axis, or other metrics.

The foregoing optimizing process also takes the intrinsic aberrations of the spectacle lens into account.

What is claimed is:

1. A method for determining an eyeglass prescription for a vision defect of an eye, the method comprising:
   mathematically varying a preliminary prescription within a target space to determine the eyeglass prescription,
   wherein mathematically varying the preliminary prescription comprises using an electronic processor to calculate, for each of multiple sets of parameter values, a value of a metric related to a caustic of a light ray passing through a corrective optic and the eye, each set of parameter values corresponding to a different prescription of a corrective optic, and
   the eyeglass prescription is selected as the prescription for which the caustic meets predetermined requirements in an area of the retina of the eye.

2. The method of claim 1, wherein mathematically varying the preliminary prescription comprises:
   a) providing refractive properties of the eye;
   b) providing the sets of parameter values describing the different prescriptions of the corrective optic;
   c) providing a method for determining from the sets of parameter values a target set which provides the eyeglass prescription for the refractive properties of the eye which were established in step a);
   d) determining, for a first set of the parameter values, values for at least two submetrics in associated different propagation stages of the light ray passing through the optical system comprising the eye and corrective optic corresponding to the prescription described by first set;
   e) determining a value of an overall metric from a weighted sum of the submetric values, the overall metric being the metric related to the caustic of the light ray passing through the corrective optic and the eye;
   f) performing the steps d) and e) for additional sets of the parameter values that are required for the determination of the target set according to the method established in step c);
   g) selecting from the sets of parameter values on which the steps d) and e) were performed the target set which delivers the overall target metric; and
   h) determining the eyeglass prescription by taking the target set selected in step g) into account.

3. The method of claim 1, wherein mathematically varying the preliminary prescription comprises:
   a) providing refractive properties of the eye;
   b) providing the sets of parameter values describing the different prescriptions of the corrective optic;
   c) providing a method for determining from the sets of parameter values a target set which provides the eyeglass prescription for the refractive properties of the eye which were established in step a);
   d) determining, for a first set of the parameter values, a value for at least one metric that characterizes the energy density of the intensity distribution in the three-dimensional space of a light bundle passing through an optical system comprising the eye and a corrective optic corresponding to the prescription described by the first set;
   e) performing the step d) for additional sets of the parameter values that are required for the determination of the target set according to the method established in step c);
   f) selecting from the sets of parameter values on which the step d) was performed the target set which delivers the overall target metric; and
   g) determining the eyeglass prescription by taking the target set selected in step f) into account.

4. The method of claim 2, wherein the refractive properties of the eye are determined based on a wavefront emanating from the eye.

5. The method of claim 4, wherein the wavefront is measured using a Shack-Hartmann method.

6. The method of claim 4, wherein the wavefront is measured using a Tscherning method.

7. The method of claim 4, wherein the wavefront is measured using a ray-tracing method.

8. The method of claim 2, wherein the refractive properties of the eye are determined by measuring the tomography of the eye.

9. The method of claim 2, wherein the sets of parameter values describing the different prescriptions of the corrective optic include values for sphere, cylinder and axis.

10. The method of claim 2, wherein the sets of parameter values describing the different prescriptions of the corrective optic include values for principal curvature radii.

11. The method of claim 2, wherein the sets of parameter values describing the different prescriptions of the corrective optic are determined from coefficients of an algebraic basis suitable for the description of the eyeglass prescription.

12. The method of claim 11, wherein the algebraic basis comprises Zernike coefficients or Taylor coefficients.

13. The method of claim 2, wherein the method for determining the target set is a Newton-Raphson method, a hill-climbing method, or a method where within a search space of parameter values, all of the sets of parameter values in the search space are examined with a view to finding an optimum.

14. The method of claim 2, wherein the submetrics are ray quality metrics.

15. The method of claim 14, wherein the ray quality metrics comprise the Strehl ratio.

16. The method of claim 14, wherein the ray quality metrics correspond to an energy enclosed within a cross-section that is traversed by the light ray.

17. The method of claim 2, wherein the submetrics are geometric metrics.

18. The method of claim 17, wherein the geometric metrics include a mean curvature of a wavefront associated with the light ray.

19. The method of claim 2, wherein all submetrics are assigned equal weight.

20. The method of claim 2, wherein at least one of the submetrics in a preferred propagation stage is given more weight than at least one of the submetrics in the propagation stages before and/or behind the preferred propagation stage.

21. The method of claim 20, wherein at least one of the submetrics in the propagation stages before or behind the preferred propagation stage are given less weight with increasing distance from the preferred propagation stage.

22. The method of claim 2, wherein the overall target metric is the maximum value of the overall metric or a value which deviates from the maximum value by a minor amount.

23. The method of claim 2, wherein the method steps a) to h) are performed for different states of accommodation of the eye.

24. The method of claim 23, further comprising:
   i) selecting a final target parameter set which delivers a final overall target metric from the overall target metrics determined for each of the different states of accommodation of the eye,
   j) determining the eyeglass prescription by taking the final target parameter sets selected in step j) into account.

25. An electronic processing system, configured to execute the method claim 1.

26. A computer-readable medium having computer executable instructions for performing claim 1.

27. The electronic processing system of claim 25, wherein executing the method of claim 1 comprises sending data over a network.

28. The electronic processing system of claim 25, comprising a computer with a display device and an input device, the computer being configured to execute one or more steps of the method.

29. An apparatus comprising:
an analyzer device comprising an electronic processor configured, during operation, to determine an eyeglass prescription for a vision defect of an eye by mathematically varying a preliminary prescription within a target space,
wherein mathematically varying the preliminary prescription comprises using the electronic processor to calculate, for each of multiple sets of parameter values, a value of a metric related to a caustic of a light ray passing through a corrective optic and the eye, each set of parameter values corresponding to a different prescription of a corrective optic, and
the eyeglass prescription is selected as the prescription for which the caustic meets predetermined requirements in an area of the retina of the eye.

30. The apparatus of claim 29, further comprising:
an input device for providing the refractive properties of the eye to the analyzer device, where the analyzer device is configured, during operation, to
i) determine values for at least two submetrics for a first set of the parameter values describing a prescription of a corrective optic, the values for the least two submetrics being determined in associated different propagation stages of a light ray passing through an optical system comprising the eye and the corrective optic corresponding to the first set of parameter values;
ii) determine a value of an overall metric from a weighted sum of the submetric values;
iii) repeat steps i) and ii) for additional sets of the parameter values, each describing different prescriptions of the corrective optic;
iv) select from the sets of parameter values on which the steps i) and ii) were performed a target set which delivers an overall target metric; and
v) determine the eyeglass prescription by taking the target set selected in step iv) into account.

31. The apparatus of claim 29, further comprising:
an input device for providing the refractive properties of the eye to the analyzer device, where the analyzer device is configured, during operation, to
i) provide the sets of parameter values describing the different prescriptions of the corrective optic;
ii) provide a method for determining from the sets of parameter values a target set which provides the eyeglass prescription for the refractive properties of the eye which were provided in step i);
iii) determines, for a first set of the parameter values, a value for at least one metric that characterizes the energy density of the intensity distribution in the three-dimensional space of a light bundle passing through the optical system comprising the eye and a corrective optic corresponding to the prescription described by the first set;
iv) performs step iii) for additional sets of the parameter values that are needed for determining the target set in accordance with the method provided in step ii);
v) select from the sets of parameter values on which step iv) was performed the target set that delivers the overall target metric; and
vi) determine the eyeglass prescription by taking the target set determined in step v) into account.

32. The apparatus of claim 30, wherein the analysis in the analyzer device takes place close to the location where the data are acquired.

33. The apparatus of claim 30, wherein the analysis in the analyzer device takes place far from the location where the data are acquired.

34. The apparatus of claim 30, wherein the input device comprises a keyboard through which data about the refractive properties of the eye can be entered.

35. The apparatus of claim 30, wherein the input device is connected to a wavefront measurement device for measuring the refractive properties of the eye.

36. The apparatus of claim 30, wherein the input device is connected to an aberrometer according to the Shack-Hartmann principle, the Tscherning method, or the ray-tracing method.

37. The apparatus of claim 30, wherein the input device is connected to a tomograph for the eye.

* * * * *

UNITED STATES PATENT AND TRADEMARK OFFICE
CERTIFICATE OF CORRECTION

| | | |
|---|---|---|
| PATENT NO. | : 7,744,217 B2 | Page 1 of 1 |
| APPLICATION NO. | : 11/840688 | |
| DATED | : June 29, 2010 | |
| INVENTOR(S) | : Jesus Miguel Guillen Cabeza | |

It is certified that error appears in the above-identified patent and that said Letters Patent is hereby corrected as shown below:

Column 3,
Line 20, delete "a" and insert --an--,

Column 6,
Line 65, delete "includes" and insert --include--,

Column 10,
Line 67, delete "claim" and insert --of claim--,

Signed and Sealed this

Twelfth Day of October, 2010

David J. Kappos
*Director of the United States Patent and Trademark Office*